US012737948B2

(12) United States Patent
Mauldin et al.

(10) Patent No.: US 12,737,948 B2
(45) Date of Patent: Sep. 15, 2026

(54) MEDICAL IMAGE AUGMENTATION

(71) Applicant: Rivanna Medical, Inc., Charlottesville, VA (US)

(72) Inventors: Frank William Mauldin, Troy, VA (US); Adam Dixon, Charlottesville, VA (US); Paul Sheeran, Waxhaw, NC (US); Kathryn Ozgun, Charlottesville, VA (US); Vicki Brothers, Elkton, VA (US)

(73) Assignee: Rivanna Medical, Inc., Charlottesville, VA (US)

( * ) Notice: Subject to any disclaimer, the term of this patent is extended or adjusted under 35 U.S.C. 154(b) by 260 days.

(21) Appl. No.: 18/608,260

(22) Filed: Mar. 18, 2024

(65) Prior Publication Data

US 2024/0312075 A1 Sep. 19, 2024

Related U.S. Application Data

(60) Provisional application No. 63/452,874, filed on Mar. 17, 2023.

(51) Int. Cl.

| | |
|---|---|
| ***G06T 12/00*** | (2026.01) |
| ***A61B 8/00*** | (2006.01) |
| ***G06T 7/00*** | (2017.01) |
| ***G06T 7/70*** | (2017.01) |

(52) U.S. Cl.

CPC ............ *G06T 12/00* (2026.01); *G06T 7/0012* (2013.01); *G06T 7/70* (2017.01); *A61B 8/5238* (2013.01); *G06T 2207/20081* (2013.01); *G06T 2207/20084* (2013.01); *G06T 2207/20092* (2013.01); *G06T 2207/20221* (2013.01); *G06T 2207/30008* (2013.01)

(58) Field of Classification Search

CPC ......... G06T 12/00; G06T 7/0012; G06T 7/70; G06T 2207/20081; G06T 2207/20084; G06T 2207/20092; G06T 2207/20221; G06T 2207/30008; G06T 5/60; G06T 5/77; A61B 8/5238

See application file for complete search history.

(56) References Cited

U.S. PATENT DOCUMENTS

| | | | | |
|---|---|---|---|---|
| 11,854,158 | B2 | 12/2023 | Reaungamornrat et al. | |
| 2018/0024341 | A1 | 1/2018 | Romanowski et al. | |
| 2018/0260950 | A1* | 9/2018 | Samset | G06T 7/0012 |
| 2019/0206052 | A1* | 7/2019 | Hu | G16H 50/30 |

(Continued)

FOREIGN PATENT DOCUMENTS

| | | | |
|---|---|---|---|
| WO | 2018048507 | A1 | 3/2018 |
| WO | 2020183799 | A1 | 9/2020 |
| WO | 2021228515 | A1 | 11/2021 |

OTHER PUBLICATIONS

Application No. PCT/US 24/20398, International Search Report and Written Opinion dated Jul. 1, 2024.

*Primary Examiner* — Vu Le
*Assistant Examiner* — Rachel Anne Ometz
(74) *Attorney, Agent, or Firm* — Woods Rogers Vandeventer Black PLC; Nathan A. Evans

(57) ABSTRACT

A computerized method for augmenting digital medical images, including an apparatus and methods utilizing a machine-learning approach for generating an augmented medical image containing features within the boundaries of the source image that are missing from or distorted in the source image.

33 Claims, 12 Drawing Sheets

700

(56) References Cited

U.S. PATENT DOCUMENTS

| | | | | |
|---|---|---|---|---|
| 2019/0237186 | A1* | 8/2019 | El-Baz | G16H 30/40 |
| 2020/0242767 | A1* | 7/2020 | Zhao | A61B 34/35 |
| 2020/0311869 | A1 | 10/2020 | Reaungamornrat et al. | |
| 2021/0045715 | A1 | 2/2021 | Mauldin et al. | |
| 2021/0390696 | A1* | 12/2021 | Iwase | G06T 7/0012 |
| 2023/0149092 | A1* | 5/2023 | Fouts | G06N 3/0464 600/300 |
| 2023/0386042 | A1* | 11/2023 | Riem | G06T 7/11 |
| 2024/0265667 | A1* | 8/2024 | Luciano | G06V 20/70 |
| 2024/0412359 | A1* | 12/2024 | Erkamp | G06T 7/0012 |
| 2025/0152243 | A1* | 5/2025 | Cheng | G06N 3/09 |
| 2025/0232571 | A1* | 7/2025 | Siemionow | G06V 10/25 |

* cited by examiner

MEDICAL IMAGE AUGMENTATION

CROSS-REFERENCE TO RELATED APPLICATION

The present application relies on the disclosures of and claims priority to and the benefit of the filing date of the following U.S. Patent Application 63/452,874, filed Mar. 17, 2023. The disclosures of that application are hereby incorporated by reference herein in their entireties.

STATEMENT REGARDING FEDERALLY SPONSORED RESEARCH

This invention was made with government support under Grant No. R44NS120798 awarded by the National Institutes of Health (NIH) National Institute of Neurological Disorders and Stroke (NINDS). The government has certain rights in the invention.

TECHNICAL FIELD

The present invention relates generally to image processing methods, apparatus, and computer-readable media for augmenting ultrasound images of anatomy.

BACKGROUND OF THE INVENTION

Medical ultrasound is commonly used to facilitate diagnostic and interventional procedures in bony anatomies. Common applications include musculoskeletal assessment of ligaments and tendons in close proximity to boney joints, injections into joint spaces, and injections into the spine and pelvis. While medical ultrasound is widely applied to these applications, it often provides incomplete or partial visualizations of the underlying anatomy, especially in boney regions. Incomplete visualizations are often the result of imaging related artifacts caused by attenuation of the ultrasound wave and the limited angular sensitivity of ultrasound imaging systems relative to bone anatomy, especially in the case of steep bone angulation found in spinal anatomy.

Incomplete ultrasound visualizations of patient anatomy can be a cause of medical errors, as misinterpretation of the underlying anatomical structures may lead to misdiagnoses or interventional procedures performed at incorrect locations. As a result, in many applications of medical imaging, signal and image processing methods are used to increase diagnostic quality by reducing the presence of artifacts in images that result from sources of interference or physics specific to the imaging modality itself. However, state-of-the-art image processing approaches and system architectures still fall short in many cases of ultrasound imaging in the vicinity of boney anatomies.

The present invention seeks to overcome two primary limitations of state-of-the-art medical ultrasound imaging procedures in boney anatomies. First, it is common for sections of contiguous bone surfaces to appear discontinuous in conventional ultrasound images due to the underlying physics of ultrasound reflection off surfaces with varying angles and densities, thereby impeding interpretation of the underlying anatomy. These artifacts are not completely resolved by approaches that involve steering the ultrasound energy across several angles relative to the anatomy. Second, the anatomical feature of interest in the medical procedure may be obscured by the presence of nearby bone and cartilage due to acoustic shadowing caused by increased attenuation of the acoustic wave.

To overcome the limitations of current state of the art image processing approaches to visualize anatomical structures, the present invention describes methods, apparatus, and non-transitory computer readable media for augmenting medical images with depictions of anatomical structures that are not contained in the source images, but can be overlaid on or otherwise added to the source images based on a priori anatomical relationships according to algorithms described herein. This approach enables improvements to ultrasound imaging technology and improved interpretation of ultrasound images, especially in anatomies containing boney structures, aiding diagnostic and interventional procedures.

Neural networks are used in medical imaging, and related art exists as described herein and below.

PCT Application No. PCT/JP2019/045301, hereby incorporated by reference herein, describes the use of medical image processing apparatus, medical image processing methods, and computer-readable storage media that use machine learning to generate an image having higher image quality than a source image, wherein image quality is defined as having low noise, high spatial resolution, and appropriate gradation to improve visualization of image features. The apparatus contains an image quality determining unit that is used to evaluate the source image properties and generate an image with quality more suitable for diagnosis. As it relates to the current invention, the apparatus of PCT/JP2019/045301 concerns improving the appearance of features that already exist in the source image, whereas the apparatus of this invention uses machine learning to augment an input image by displaying features missing from, obscured, and/or distorted in the input image, by way of example.

U.S. application Ser. No. 16/773,213, hereby incorporated by reference herein, describes systems and methods for medical image enhancement, particularly focusing on generating augmented medical images with expanded field of view using trained machine learning models. The process involves receiving an initial medical image, generating an augmented image with a larger field of view, optionally refining the augmented image, and outputting the refined medical image for display, storage, or transmission. As it relates to the current invention, the methods and systems of U.S. Ser. No. 16/773,213 concern generating imaging content in a region beyond the borders of the imaging field, whereas the methods this invention, in aspects, use machine learning to augment content (e.g., human or animal anatomy) of the source image operated on by the machine learning model.

PCT Application No. PCT/US2017/042136, incorporated herein by reference, describes systems, methods, and computer readable media for generating synthetic images of anatomical portions based on origin images acquired using a first imaging modality (e.g., MRI) and predicting synthetic images resembling a second imaging modality (e.g., CT). The method involves receiving origin images and a trained convolutional neural network (CNN) model, converting origin images to synthetic images through the CNN model, and storing the synthetic images. In the current invention as described herein, the machine learning model is trained to generate a synthetic image including anatomy that is missing from and/or distorted in the source image.

PCT Application No. PCT/US2017/042136, incorporated herein by reference, describes apparatuses, systems, and techniques to infer the boundaries of objects obscured by other objects in an input image, or to complete the boundaries of objects that fall outside of the captured region, based on the use of neural networks. In embodiments, PCT/

US2017/042136 describes generating completed representations of objects that are partially obscured by other objects in the image, or that partially fall outside of the boundaries of the image. However, PCT/US2017/042136 requires that an encoder of the one or more neural network model is trained using training data generated based on an output of a decoder of the one or more neural networks. According to embodiments the current invention as described herein, the invention allows for completion of features that are missing from, obscured, and/or distorted within the input image boundaries as a result of artifacts related to acoustic imaging physics, rather than simply obscuration due to the presence of other physical objects in the path.

PCT Application No. PCT/EP2021/060286, incorporated herein by reference, describes medical systems and a computer program that includes an image generating neural network capable using a source image produced by an imaging device having a first configuration to produce a synthetic image that emulates the appearance of an image produced by a device having a second configuration. PCT/EP2021/060286 primarily aims to reduce artifacts, image corruption, and accelerate image acquisition in magnetic resonance imaging systems by reconstructing images from sub-sampled data while emulating the appearance of highly sampled data. PCT/EP2021/060286, however, is restrictive to neural network models that operate on k-space data from magnetic resonance imaging machines and does not teach that features missing from, obscured, and/or distorted in the input image can be included in a treated image according to the invention as described herein.

SUMMARY OF THE INVENTION

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

In aspects, the invention can be partitioned into four exemplary units: the source image receiving unit, the synthetic image generation unit, the augmentation unit, and the output unit. First, the source image receiving unit receives medical image data containing an anatomical portion of a subject, the synthetic image generation unit uses a trained machine learning model to generate a synthetic image based on the source image such that the synthetic image contains one or more anatomical features that cannot be visualized (and/or are distorted visually) on the source image due to physical or other limitation associated with the medical imaging modality, the augmentation unit combines blends, or overlays information from the source image and the synthetic image to produce an augmented image, and the output unit transfers the augmented image beyond the apparatus, such as to a user interface (e.g., a display screen).

In embodiments, the invention may contain additional exemplary units, which may include a classification/segmentation unit that classifies image regions on the basis of expected anatomy, a registration unit that compares the synthetic image to one or more a priori anatomical models of the underlying anatomy, and a quantification unit that algorithmically converts information from the registration unit and/or classification/segmentation unit into quantitative measures of the anatomical portion of the subject that may be relevant to diagnosis or procedure guidance.

In embodiments, the present invention overcomes limitations of existing image processing approaches by augmenting the medical image with computer-generated depictions of anatomical structures that are not contained within the ultrasound image (or are in some way distorted within the ultrasound image), but whose presence can be automatically overlaid or otherwise added to the ultrasound image based on a priori anatomical relationships with respect to, for example, the part of the body or the anatomy being imaged. This approach enables improved interpretation of images, especially those containing boney anatomies, which is critical for performing diagnostic and interventional procedures.

BRIEF DESCRIPTION OF THE DRAWINGS

The accompanying drawings illustrate certain aspects of some of the embodiments of the present invention and should not be used to limit or define the invention. Together with the written description the drawings serve to explain certain principles of the invention. For a fuller understanding of the nature and advantages of the present technology, reference is made to the following detailed description of preferred embodiments and in connection with the accompanying drawings, in which.

DETAILED DESCRIPTION OF VARIOUS EMBODIMENTS OF THE INVENTION

Figure 1A:
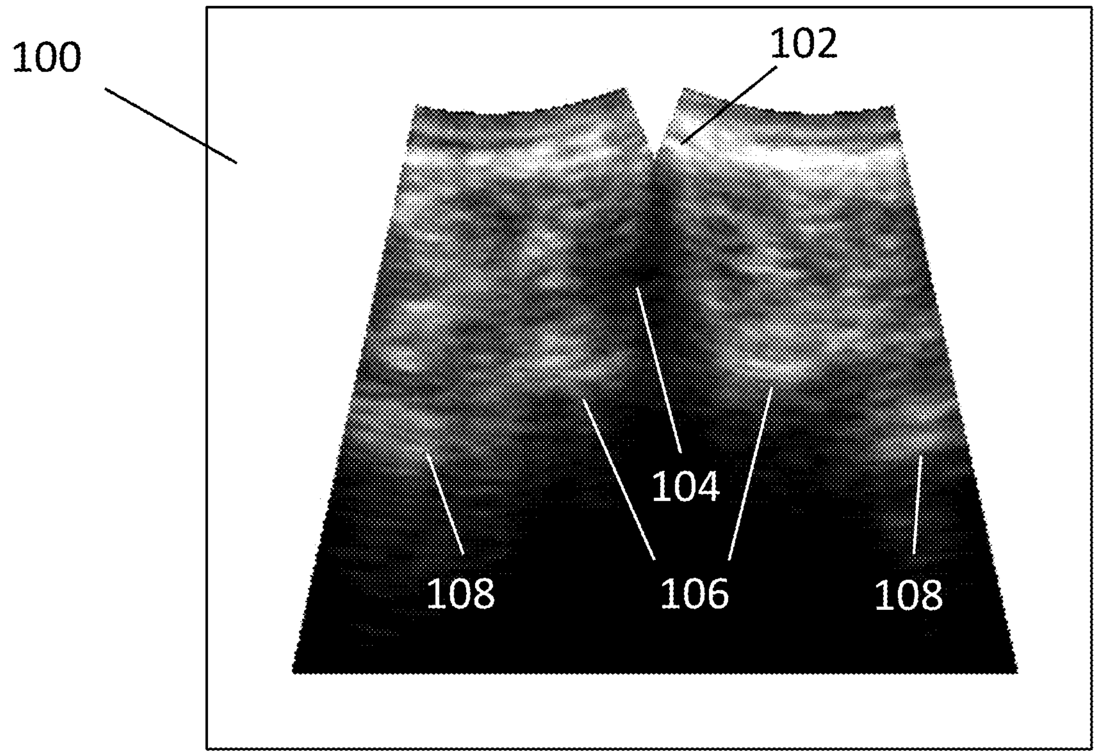
FIGS. 1A-B depict an exemplary medical image of an anatomical portion of a subject and an anatomical model registered to the subject anatomy.

The present disclosure describes various systems and methods for augmenting medical ultrasound images using one or more neural networks and image processing approaches. The neural network approach may be applied to generate synthetic medical images derived from source images acquired by an imaging modality, such that the synthetic medical images have the appearance of being from the same imaging modality as the source images. The imaging modality of the source images may be one of, or a fusion of, ultrasound, MRI, CT, OCT, X-Ray, photoacoustic imaging, or other medical imaging modalities. In other embodiments, one or more neural networks may be applied to derive anatomical classification maps that label regions of anatomy in images based on the input of a synthetic medical image produced by a neural network approach. In preferred embodiments, the synthetic image back-fills areas of the ultrasound image with anatomical information, generated by a trained machine learning model, that was not captured in the original ultrasound image acquisition, but whose position (such as approximate position) in the ultrasound image can be determined based on known anatomical relations. In other embodiments, image processing methods are used to register the synthetic image with one or more a priori anatomical models of the underlying anatomy in order to determine one or more probability that the source image coincides with a target anatomy and/or other anatomy in the body region. In other embodiments, image processing methods are used to quantify information generated by classifying or segmenting regions of the synthetic image, or registering regions of the synthetic image against one or more a priori anatomical models. In preferred embodiments, image processing methods are used to generate an augmented medical image that may include blending, overlaying, or compounding of the source and synthetic images, enhancement of the source and synthetic images based on classification or segmentation results, graphical annotations that depict quantitative aspects drawn from classifying, segmenting, or registering the synthetic data, and/or graphical overlays that depict a priori anatomical models relative to the source and synthetic images, like vector art or template overlays.

In embodiments of the present invention for medical applications of ultrasound imaging described herein, an objective of the invention is to enhance or augment the ultrasound image with anatomical information that is not captured directly within the raw underlying ultrasound data, and/or with anatomical information that is not adequately captured directly within the underlying ultrasound data, such as anatomical information that is being captured but distorted in some manner. In embodiments, additional objectives include, but are not limited to, planning of interventional procedures to target anatomical structures that are not visualized within the underlying ultrasound data. In embodiments, the invention may be applied to two-dimensional ultrasound image acquisitions or three-dimensional ultrasound acquisitions to facilitate assessment of large sections of patient anatomy, or any sections of patient anatomy, from large to small. The present invention can be utilized, in a preferred embodiment, with systems and methods previously disclosed by Mauldin et al. (PCT/US2011/022984, PCT/US2014/018732, PCT/US2017/047472, and PCT/US2019/1012622), which are hereby incorporated by reference herein, for automated detection of boney anatomy and registration against a priori anatomical models.

Figure 1B:
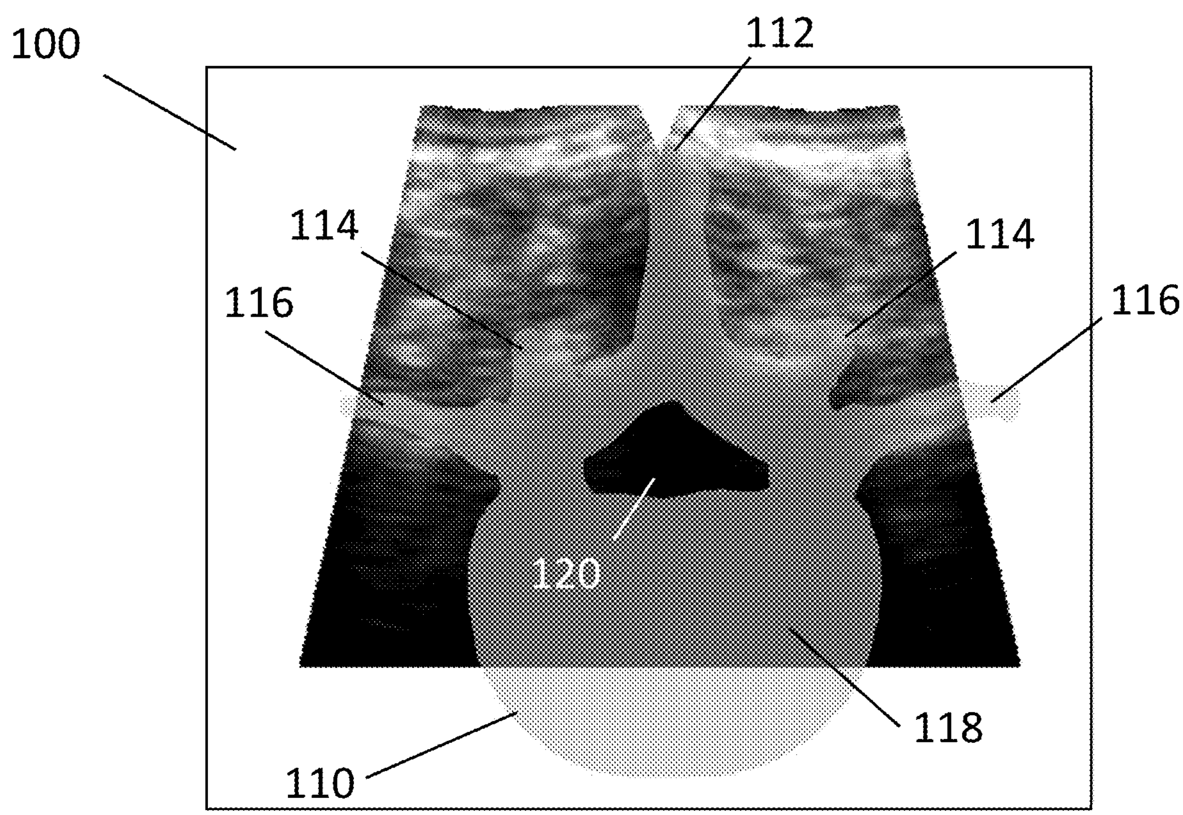

In FIG. 1A, an exemplary ultrasound image 100 depicts an anatomical image of the lumbar spine of a patient (or any other subject). Multiple tissue types are present in the ultrasound image 100, including bright features associated with boney structures of the spine. These features include, but are not limited to, the spinous process tip 102, the articular processes 106, and the transverse processes 108. Although the general outline of the spinal anatomy can be detected by trained readers, bone segments that connect the spinal anatomy are obscured or only partially captured due to the limitations involved with sound propagation physics, and limited angular sensitivity of ultrasound imaging transducers. One such bone segment is the lateral edge of the spinous process 104, which does not return sufficient energy intensity to be distinguished in the ultrasound image 100, as well as any structures below the most superficial bone surfaces. FIG. 1B depicts the same ultrasound image 100 of the lumbar spine of a patient (or any other subject) and overlaid upon the ultrasound image 100 is an anatomical model 110 depicting a cross-section of the lumbar spine at the spinous process. Evident in the anatomical model 110 are connecting regions of bone between the spinous process 112, articular processes 114, and transverse processes 116, as well as features that cannot be distinguished on the ultrasound image 100 due to acoustic attenuation, including the vertebral body 118 and spinal canal 120.

Figure 2:
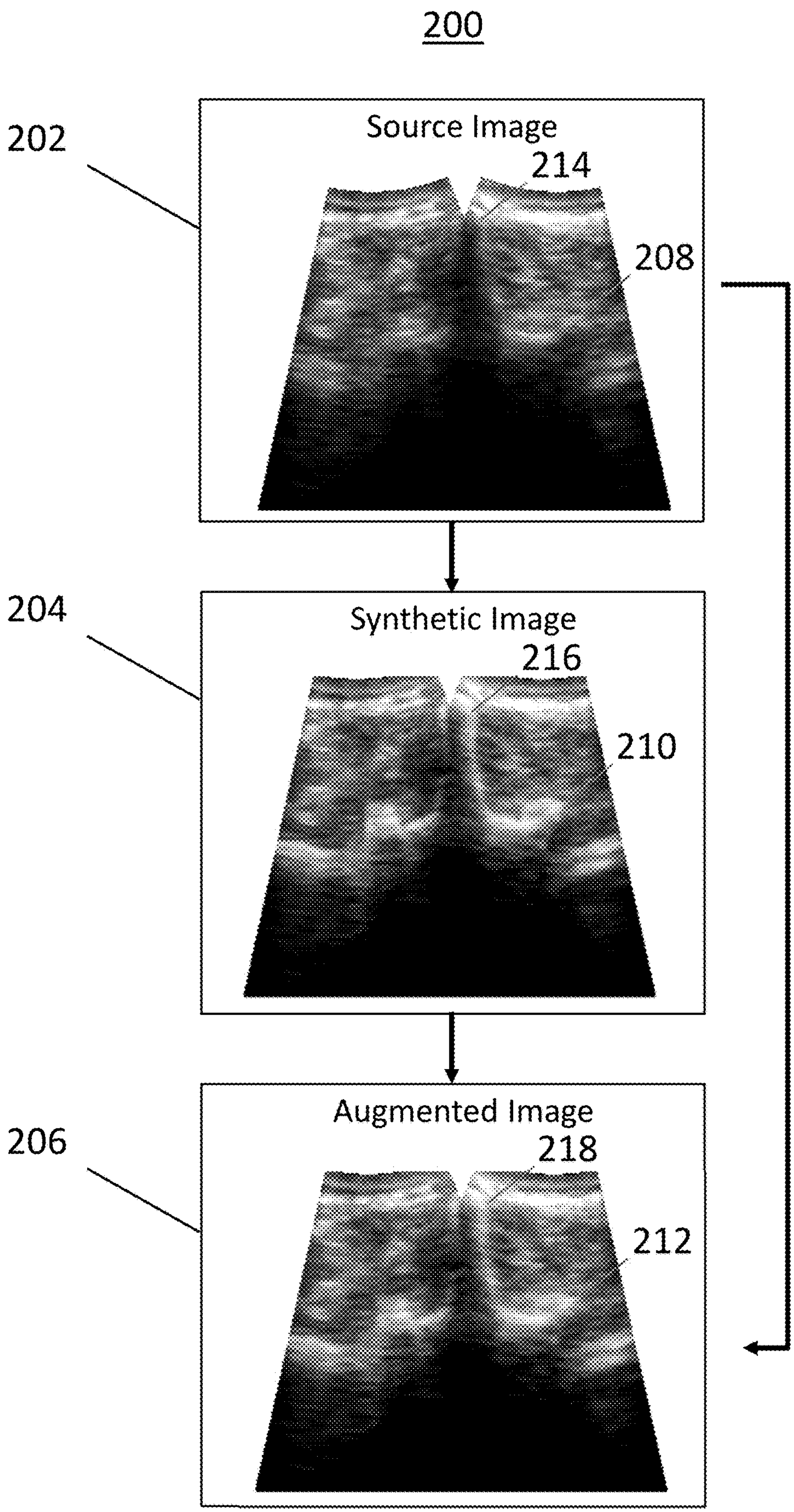
FIG. 2 shows an illustrative high-level workflow for augmenting a medical image of an anatomical portion of a subject, and exemplary augmentations of ultrasound images of a lumbar spine, in accordance with one or more embodiments.
Figure 3:
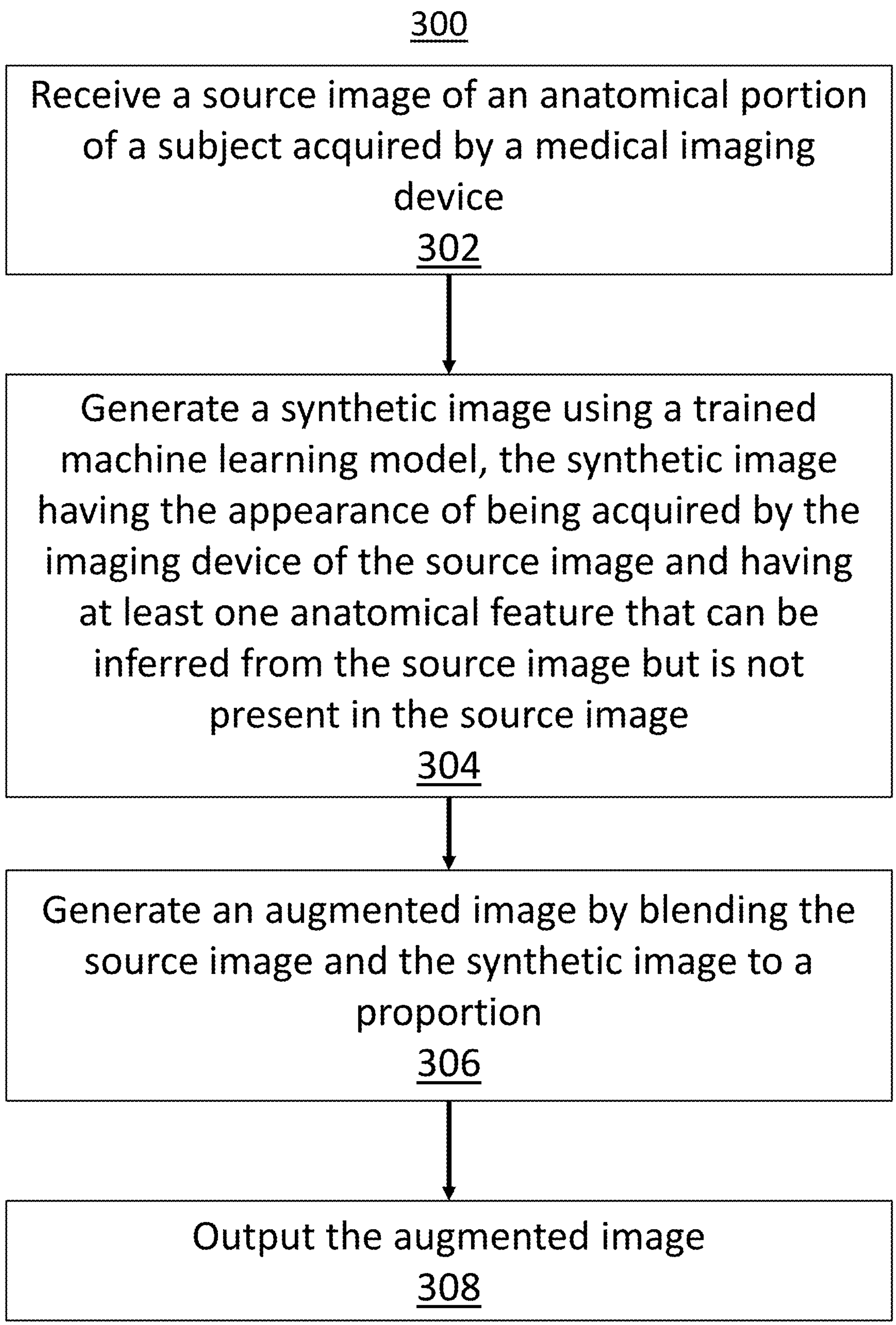
FIG. 3 depicts a high level workflow for augmenting a medical image through use of a trained machine learning model that adds anatomical information not found in (or distorted in) the source medical image, in accordance with one or more embodiments.

FIG. 2 depicts an illustrative high-level workflow 200 for augmenting a medical imaging according to one or more embodiments, and FIG. 3 depicts a method 300 for implementing the high-level workflow 200 found in FIG. 2. In the following description, the steps of the method described in FIG. 3 are detailed, with example embodiments in FIG. 2.

In an exemplary embodiment, the method 300 comprises a first step 302 of receiving a source image of an anatomical portion of a subject acquired by a medical imaging device. An exemplary source image 202 is shown in FIG. 2 and depicts several visible regions of boney anatomy that include the spinous process tip 214 and articular process 208. The source image 202 may be an image from any medical imaging modality, including but not limited to ultrasound, CT, X-Ray, MRI, PET, SPECT, photoacoustics, or any other medical imaging modality or fusion of two or more imaging modalities. The source image 202 may comprise a single 2-dimensional imaging frame, a time-series of 2-dimensional imaging frames, or a 3-dimensional dataset. The source image 202 may be transferred directly from computer memory on the medical imaging device that acquired the source image 202 or may be transferred from computer memory of an apparatus other than the medical imaging device that acquired the source image 202.

A second step 304 of an exemplary embodiment in FIG. 3 involves generating a synthetic image using a trained machine learning model, the synthetic image, in aspects, having the appearance of being acquired by the imaging device of the source image 202 and, in aspects, having at least one anatomical feature that can be inferred from the source image 202, such as by comparison between the source image 202 and at least one a priori anatomical model. An exemplary synthetic image 204 is shown in FIG. 2 and depicts several synthetic anatomical features not present in the source image 202, including an enhanced, contiguous border between the spinous process tip 216 and articular process 210. The synthetic anatomical features may be of any size, shape, or intensity, depending on the anatomy being imaged, but, in a preferred embodiment, should be contained within the boundaries of the source image 202. The trained machine learning model may be comprised of one or more generative adversarial networks (GANs), or any other machine learning model capable of generating 2D or 3D synthetic medical images. The machine learning model architecture may comprise a U-Net, spatially aware autoencoders, context aware autoencoders, long-term short memory (LTSM), and/or recurrent neural networks (RNNs), as well as any other model architecture element advantageous for the purpose of generating synthetic anatomical features from input images.

A third step 306 of an exemplary embodiment in FIG. 3 involves generating an augmented image by blending the source image 202 and synthetic image 204 to a proportion. An exemplary augmented image 206 is shown in FIG. 2 and depicts a weighted averaging of the source image 202 and synthetic image 204 to preserve a look more consistent with the source imaging modality. In an embodiment, the blending may comprise a mathematical averaging technique, such as minimum, harmonic mean, quadratic mean, or maximum of the source image 202 and synthetic image 204. In an embodiment, the blending may comprise a weighted blending of the source image 202 and synthetic image 204 based on predetermined weighting coefficients. In an embodiment, the blending may comprise an adaptive approach that combines portions of the source image and the synthetic image based on quantitative image metrics, such as similarity metrics, or based on confidence or probability metrics from the trained machine learning model.

A fourth step 308 of an exemplary embodiment in FIG. 3 involves outputting the augmented image, which may comprise transfer to a display on the acquisition device, display on an apparatus other than the acquisition device, or storage in computer memory on the acquisition device or an apparatus other than the acquisition device, by way of example only.

Figure 4:
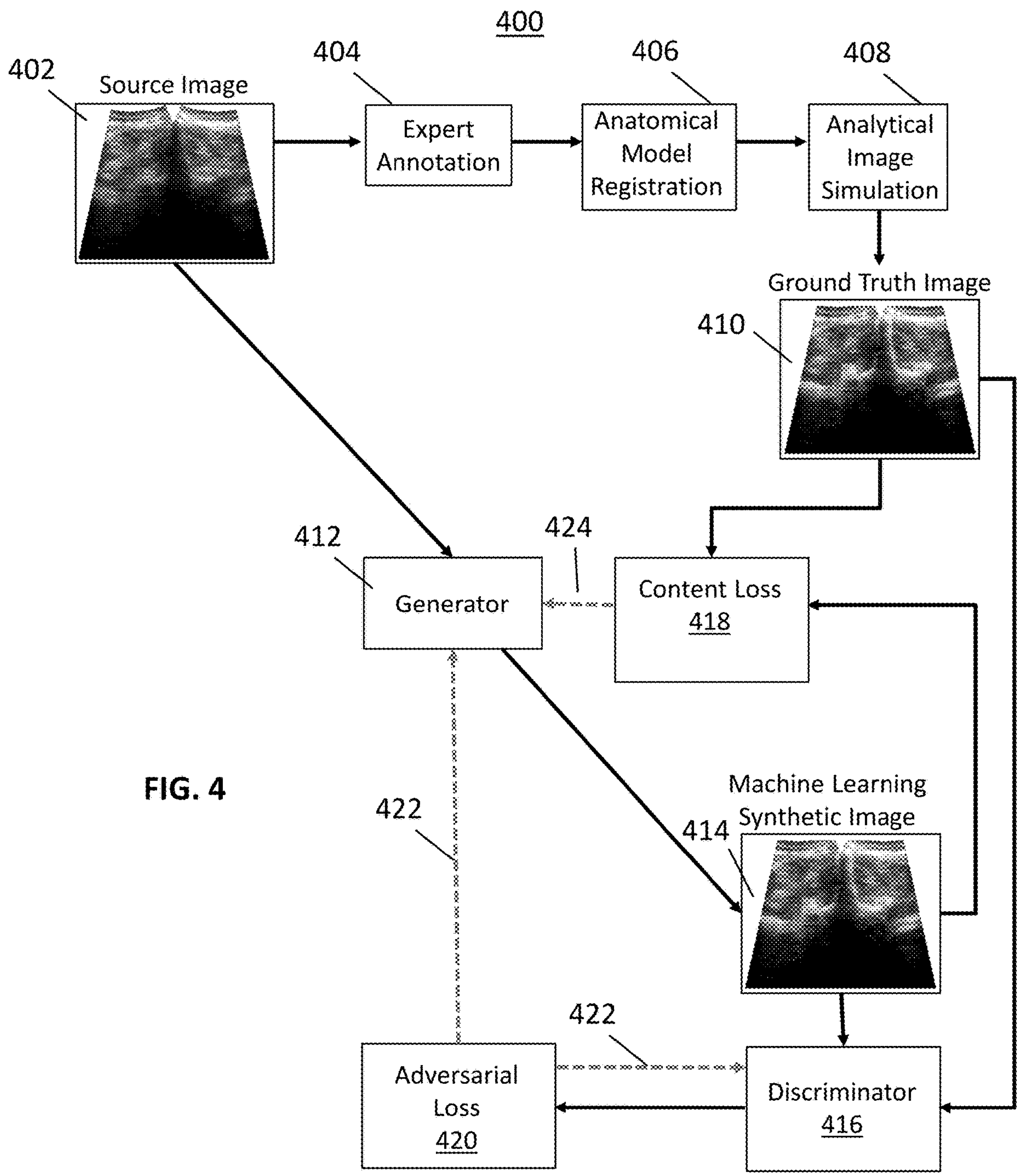
FIG. 4 depicts a functional block diagram for training a generative adversarial network (GAN) for generating a synthetic medical image, in accordance with one or more embodiments.

In an exemplary embodiment depicted in FIG. 4, the machine learning model is trained through a generative adversarial network (GAN) architecture 400. The GAN architecture generates a synthetic image 414 from the input image 402 via a generator 412. A discriminator 416 compares the synthetic image 414 and a ground truth image 410 to determine an adversarial loss function 420. Both the generator 412 and discriminator 416 are trained in conjoint with content loss 420 and adversarial loss 420 functions as feedback 422, 424 to improve performance of both the discriminator 416 and generator 412 simultaneously. In aspects, once training is complete, only the generator 412 is used for synthetic image generation. In an embodiment, the training data consists of pairs of source images 402 and synthetic ground truth images 410 produced by simulations. The ground truth images 410 may be generated by a process involving expert annotation 404 of the anatomical features that are visible in the source image 402, comparison with at least one a priori anatomical model 406, and analytical image simulation 408 of the ground truth image based on inputs in the form of at least one expert annotation 404 and comparison with at least one a priori anatomical model 406. The analytical image simulation 408 may comprise physical simulations, such as finite-element approaches, image processing approaches, such as adding, enhancing, or removing features while preserving noise and artifacts characteristic of the imaging modality, or any other suitable approach.

Figure 5:
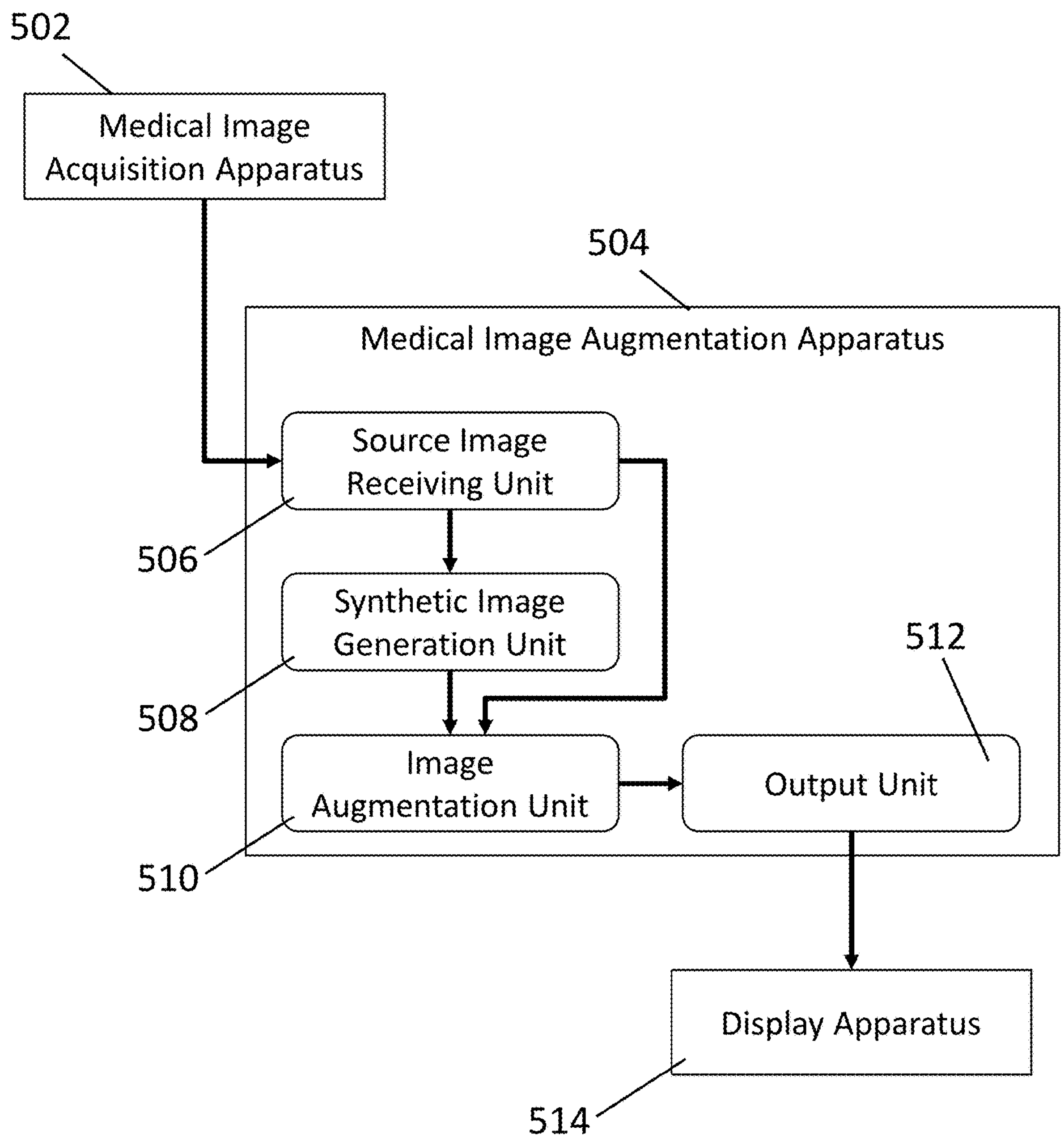
FIG. 5 illustrates an example of a schematic configuration of a medical image augmentation apparatus, according to an embodiment.

In an embodiment, a medical image augmentation apparatus 504 employing the method of FIG. 3 is depicted in FIG. 5. The medical image augmentation apparatus 504 may be a unit of the medical imaging device that acquires a source image or may be a unit of an apparatus other than the medical imaging device that acquires a source image. A medical image acquisition apparatus 502 may be an imaging apparatus or may be a medical image storage apparatus. The medical imaging acquisition apparatus 502 acquires a source image and transfers the source image to a source image receiving unit 506. The source image receiving unit 506 transfers the source image to a synthetic image generation unit 508, wherein the methods involved with synthetic image generation 304 are executed, and an image augmentation unit 510. The image augmentation unit 510 receives the synthetic image generated by the synthetic image generation unit 508 and executes the methods involved with image augmentation 306. The augmented image is transferred to the output unit 512, which executes the methods involved with outputting the augmented image 308. In an embodiment, the output unit 512 transfers the augmented image to a display apparatus 514 that conveys the augmented image to a user and/or an observer. In other embodiments, the output unit 512 transfers the augmented image to computer memory for storage.

Figure 6:
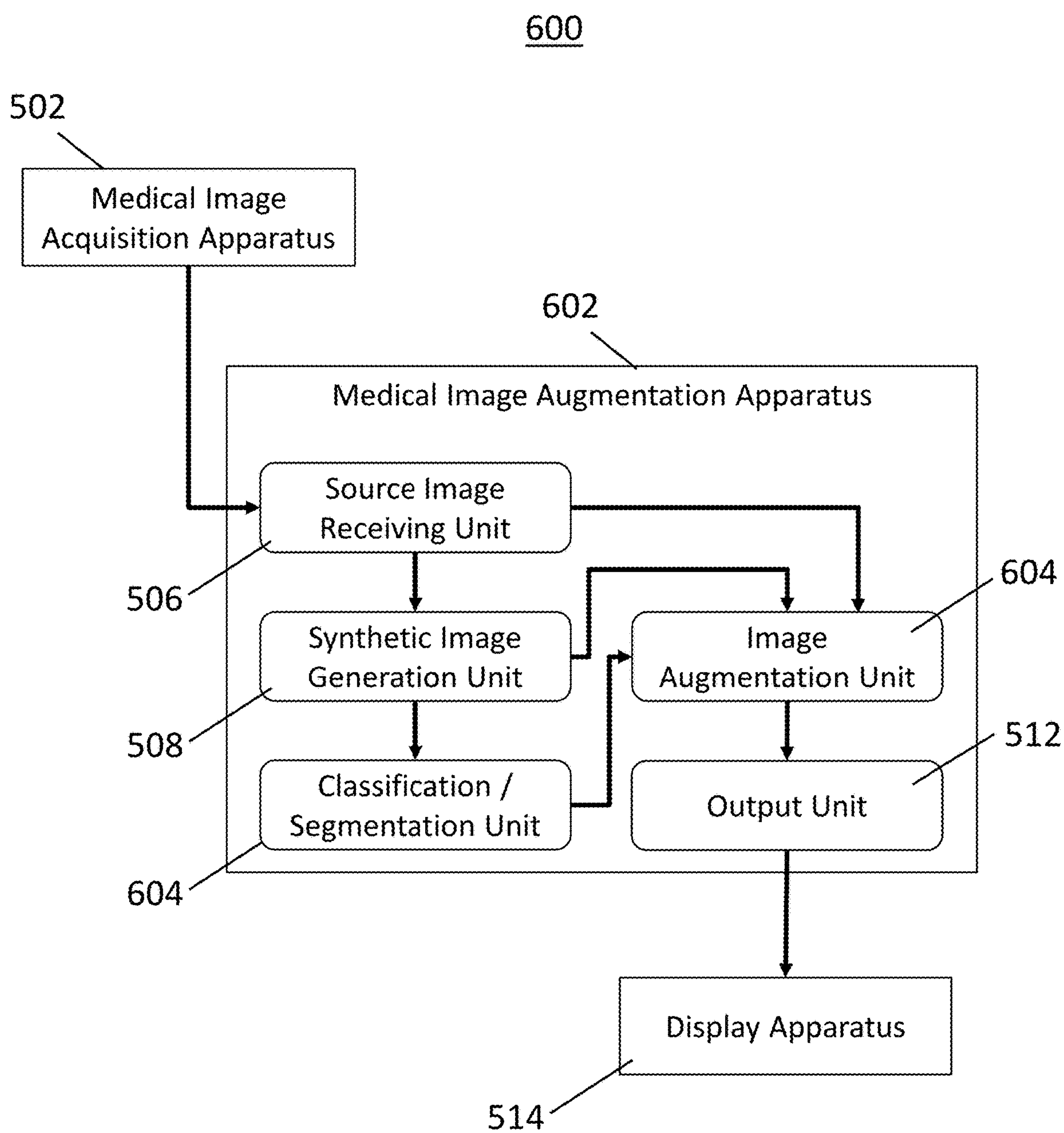
FIG. 6 illustrates an example of a schematic configuration of a medical image augmentation apparatus, according to an embodiment.

In an embodiment depicted in FIG. 6, the medical image augmentation apparatus 602 comprises the elements of the medical image augmentation apparatus 502 of FIG. 5, further comprising a classification/segmentation unit 604. In an embodiment, the classification/segmentation unit 604 receives the generated synthetic image from the synthetic image generation unit 508 and classifies and/or segments the synthetic image to produce a classification map that assigns each pixel, for example, in the synthetic image to one of several predetermined classes based on the anatomy being imaged. The classification/segmentation unit 604 may comprise a trained machine learning model to perform semantic segmentation and/or classification, which may be comprised of one or more generative adversarial networks (GANs), or any other machine learning model capable of segmenting and/or classifying anatomical features in the 2D or 3D synthetic images described herein. The classification/segmentation machine learning model architecture may comprise a U-Net, spatially aware autoencoders, context aware autoencoders, long-term short memory (LTSM), and/or recurrent neural networks (RNNs), as well as any other model architecture element advantageous for the purpose of generating classifications and segmentations of anatomical features from the synthetic images described herein. In an embodiment, the classification/segmentation unit may comprise analytical algorithms that segment and/or classify anatomical features on the basis of image properties, which may include comparison of local, regional, and/or global measures of intensity, variation, texture, or other appropriate metrics. The augmentation unit 604 receives the source image 202, the synthetic image 204 generated by the synthetic image generation unit 508, and the classification and/or segmentation maps generated by the classification/segmentation unit 604 and executes the methods involved with image augmentation 306, further comprising methods to incorporate the classification and/or segmentation maps into the augmented image. In embodiments, the classification and/or segmentation maps may be incorporated into the augmented image by altering the intensity (or other properties) of pixels associated with predetermined classifications, and/or by altering the intensity (or other properties) of pixels falling outside of predetermined classifications. In embodiments, the classification and/or segmentation maps may be incorporated into the augmented image by altering the hue and/or saturation of pixels associated with predetermined classifications, although alterations other than hue and/or saturation are envisioned. In embodiments, the image augmentation unit 808 may adjust the proportion of augmentation contributed by the classification and/or segmentation maps based on algorithms comparing local, regional, and/or global measures of intensity, variation, texture, or other appropriate metrics of the source image and/or synthetic image.

Figure 7:
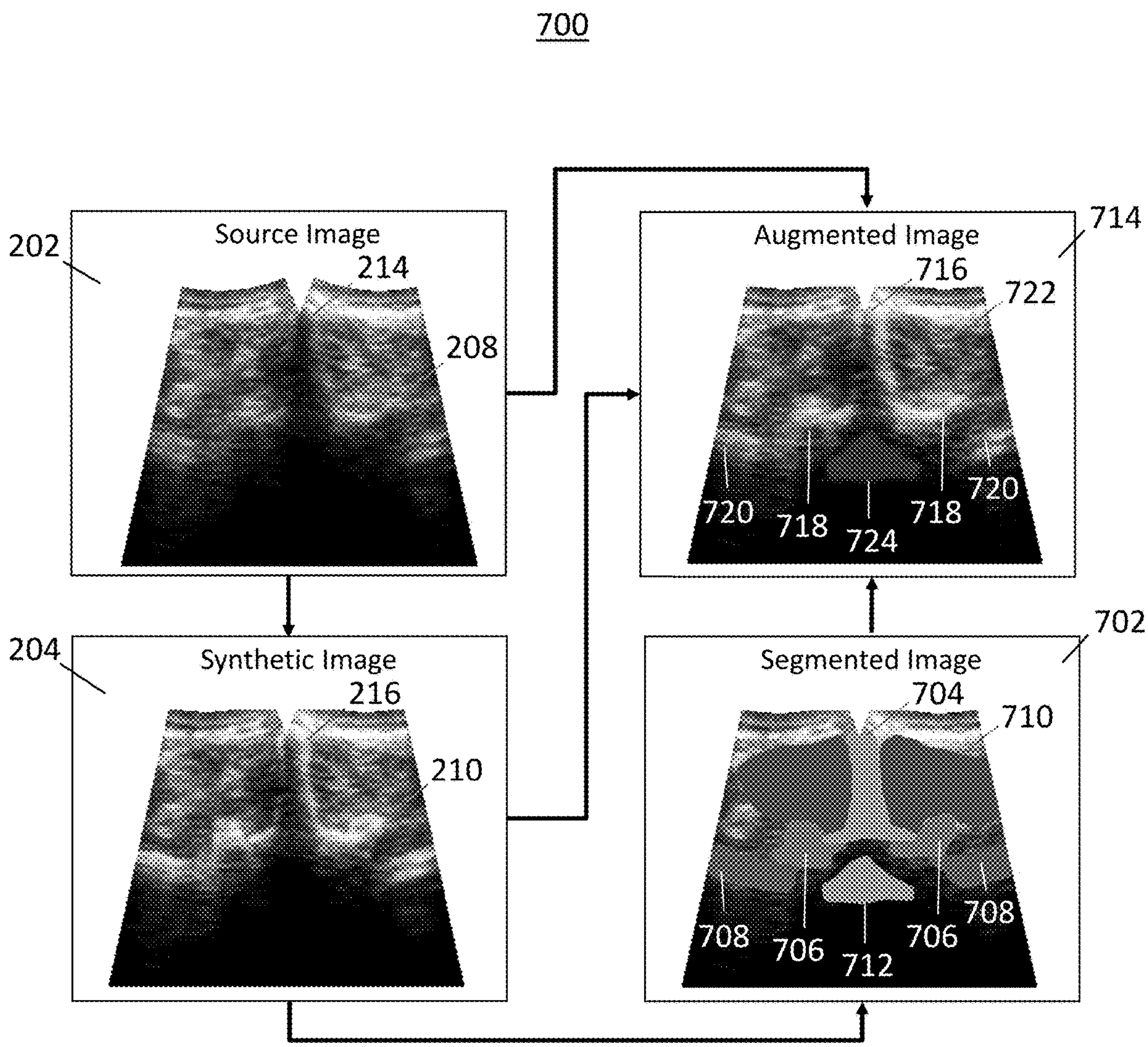
FIG. 7 depicts an illustrative high-level workflow for augmenting a medical image of an anatomical portion of a subject, and exemplary augmentations of ultrasound images of a lumbar spine, in accordance with one or more embodiments.

FIG. 7 depicts an illustrative high-level workflow 700 for augmenting medical imaging according to one or more embodiments of the medical imaging augmentation apparatus 602 and associated methods depicted in FIG. 6 and described above and herein. An exemplary source image 202 is shown in FIG. 2 and depicts several visible regions of boney anatomy that include the spinous process tip 214 and articular process 208. The source image 202 may be an image from any medical imaging modality, including ultrasound, CT, X-Ray, MRI, PET, SPECT, photoacoustics, or any other medical imaging modality or fusion of two or more imaging modalities. The source image 202 may comprise a single 2-dimensional imaging frame, a time-series of 2-dimensional imaging frames, or a 3-dimensional dataset. The source image 202 may be transferred directly from computer memory on the medical imaging device that acquired the source image 202 or may be transferred from computer memory of an apparatus other than the medical imaging device that acquired the source image 202. The source image 202 is received by the source image receiving unit 506 depicted in FIG. 5 and processed by the source image receiving method 302 depicted in FIG. 3. The synthetic image generation unit 508 uses the source image 202 as input to generate a synthetic image 204 containing enhanced appearance of the spinous process tip 216 and articular processes, as well as other boney anatomy, according to the synthetic image generation methods 304 described in FIG. 3. The classification/segmentation unit 604 processes the synthetic image 204 according to methods described herein to generate a classification map 702 that assigns one or more pixels or voxels (or regions or subregions) in the synthetic image 204 to a unique anatomical classification. In an embodiment, the classification map 702 may comprise anatomical regions associated with the lumbar spine, such as one or more spinous process 704, one or more muscle 710, one or more articular process 706, one or more transverse process 708, the spinal canal 712, one or more blood vessel, one or more adipose tissue region, one or more tendon or ligament, as well as other anatomical regions. In embodiments, the classification map 702 may comprise anatomical regions associated with the lumbar spine, thoracic spine, cervical spine, chest, hip, pelvis, leg, ankle, foot, arm, wrist, hand, or any body part, region, or anatomy, as well as other anatomical features associated with the anatomical region in the source image 202. The image augmentation unit 604 uses the source image 202, the synthetic image 204, and the classification map 702 as input to generate an augmented image 714 according to the image augmentation methods 306 described in FIG. 3 and further comprising methods associated with the classification/segmentation unit 604 described herein. In an embodiment, the augmented image 714 overlays the classification map 702 with a blending of the source image 202 and the synthetic image 214 to alter intensity, hue, saturation, and/or other image properties, of regions associated with predetermined classifications, which may include one or more spinous process 716, one or more muscle 722, one or more articular process 718, one or more transverse process 720, the spinal canal, one or more blood vessel, one or more adipose tissue region, one or more tendon or ligament, as well as other anatomical features associated with the anatomical region in the source image 202.

Figure 8:
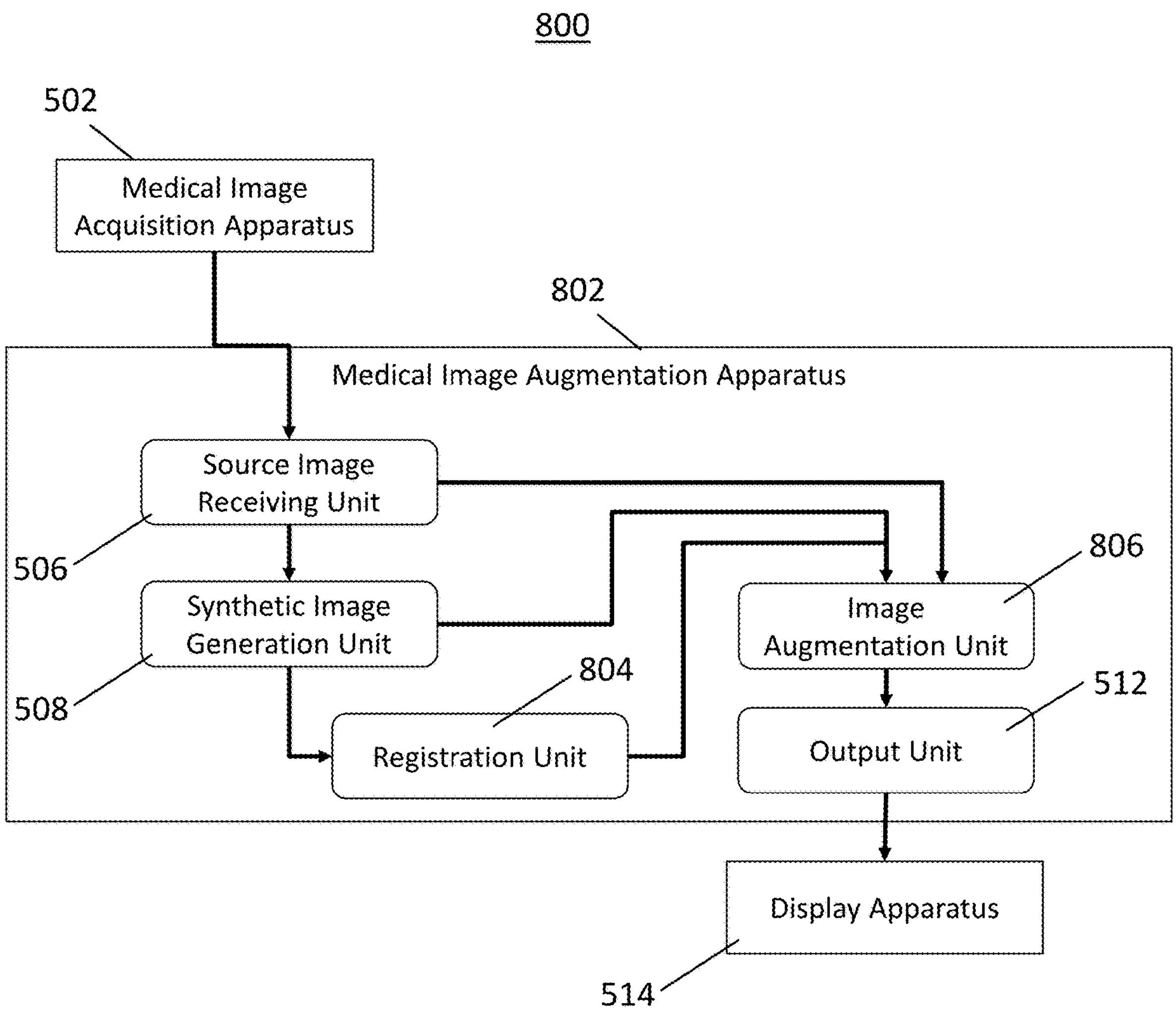
FIG. 8 illustrates an example of a schematic configuration of a medical image augmentation apparatus, according to an embodiment.

In an embodiment depicted in FIG. 8, the medical image augmentation apparatus 802 comprises the elements of the medical image augmentation apparatus 502 of FIG. 5, further comprising a registration unit 804. In an embodiment, the registration unit 804 receives the generated synthetic image 204 from the synthetic image generation unit 508 and spatially aligns the synthetic image 204 to an a priori model of the underlying anatomy 106, the underlying model being stored in memory and formatted as a full 3D model, a sparse point set model, or other model format compatible with digital storage. In an embodiment, the registration unit 804 improves and/or optimizes the spatial alignment between the synthetic image 204 and an a priori model of the anatomy being imaged. The a priori model may be a single model derived from a three-dimensional clinical dataset (e.g., computed tomography or magnetic resonance imaging) or an idealized CAD model, or it could be a library of multiple a priori models. Functionally, the registration unit 804 applies a mathematical optimization algorithm (e.g., gradient descent, simplex search, affine transforms, spline transforms, etc.) to minimize the error in pixel-to-pixel alignment between the a priori model and the synthetic image 204. In embodiments, the registration unit 804 may compare the synthetic image 204 with a full a priori model or a sparse, down-sampled a priori model. In aspects, the outputs of the registration unit 804 are position and scale vectors that optimize the alignment between the synthetic image 204 and the one or more a priori models and provide a spatial relationship between informational content contained in the synthetic image 204 and the one or more a priori models. The augmentation unit 806 receives the source image 202, the synthetic image 204 generated by the synthetic image generation unit 508, and the outputs of the registration unit 804, and executes the methods involved with image augmentation 306, further comprising methods to incorporate the registration information into the augmented image. In an embodiment, the image augmentation unit 806 utilizes outputs of the registration unit 804 to produce computer-generated graphics of anatomical structures that are merged, overlaid, blended, or otherwise incorporated, into the combined source image 202 and synthetic image 204. In an exemplary embodiment, the augmentation unit 806 produces a labeled, digitized model of the anatomy contained within the augmented image from the results provided by the registration unit 804. In this context, labeled pixels in two-dimensional images or voxels in three-dimensional datasets correspond to anatomical features, including but not limited to bone surfaces, muscles, adipose tissues, and blood vessels. In an exemplary embodiment, the augmentation unit 806 adds or fuses computer-generated graphical information to the augmented image, the computer-generated graphical information having been derived from the aligned a priori model. In a non-limiting example, the augmentation unit 806 may add a graphical overlay or fuse additional computer-generated graphic information into the augmented image that imparts information related to the position of a spine, muscles, and adipose tissue in the image. This computer-generated graphical information could be vector line art, graphical art, or pictorial depictions of a spine derived from medical images of various medical imaging modalities, such as CT, MRI, or X-ray. In an exemplary embodiment, the augmentation unit 806 generates an image composed of two non-overlapping images, one of the non-overlapping images comprised of a blending of the source image 202 and synthetic image 204, and the other non-overlapping image comprised of computer-generated graphical information of the anatomy or a blending of computer-generated graphical information of the anatomy, the source image 202, and the synthetic image 204.

Figure 9:
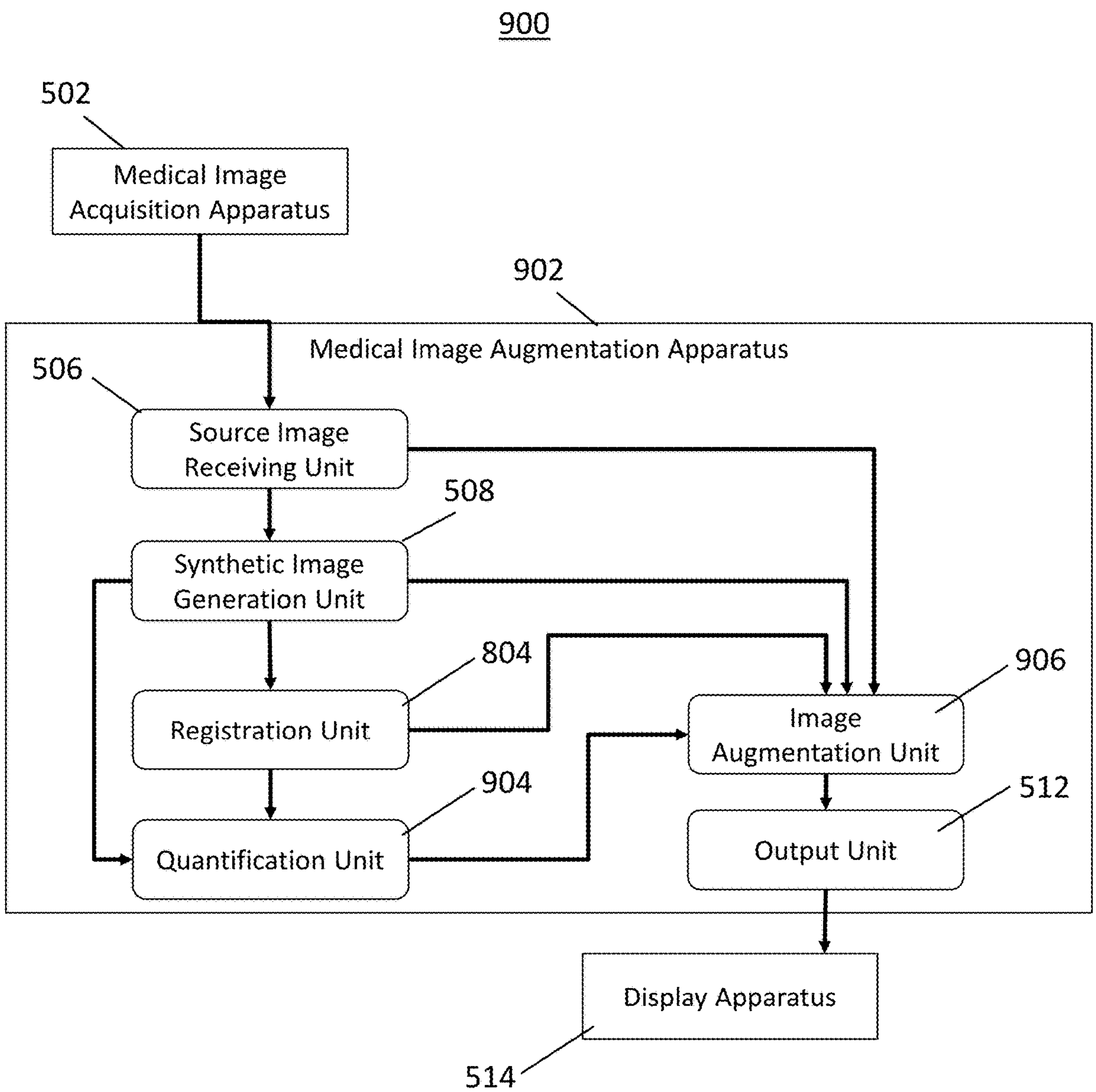
FIG. 9 illustrates an example of a schematic configuration of a medical image augmentation apparatus, according to an embodiment.

In an embodiment depicted in FIG. 9, the medical image augmentation apparatus 902 comprises the elements of the medical image augmentation apparatus 802 of FIG. 8, further comprising a quantification unit 904. In embodiments, the quantification unit 904 receives one or more synthetic image 204 generated by the synthetic image generation unit 508 as well as the output of the registration unit 804, and processes these inputs to generate quantitative data relevant to the subject anatomy contained in the source image 202. In an embodiment, the quantification unit 904 process these inputs to generate metrics associated with the position of the anatomy contained in the source image 202, which may include depth, size, or orientation of predetermined features within the anatomy, positional alignment of features in the anatomy relative to features of the imaging device, or confidence measures associated with positioning and/or presentation of features contained in the source image 202. The image augmentation block 906 comprises the functionality of the image augmentation block 806 of FIG. 8, further comprising methods to integrate results from the quantification unit 904 into the augmented image, such as through graphical overlays or other suitable approaches.

Figure 10:
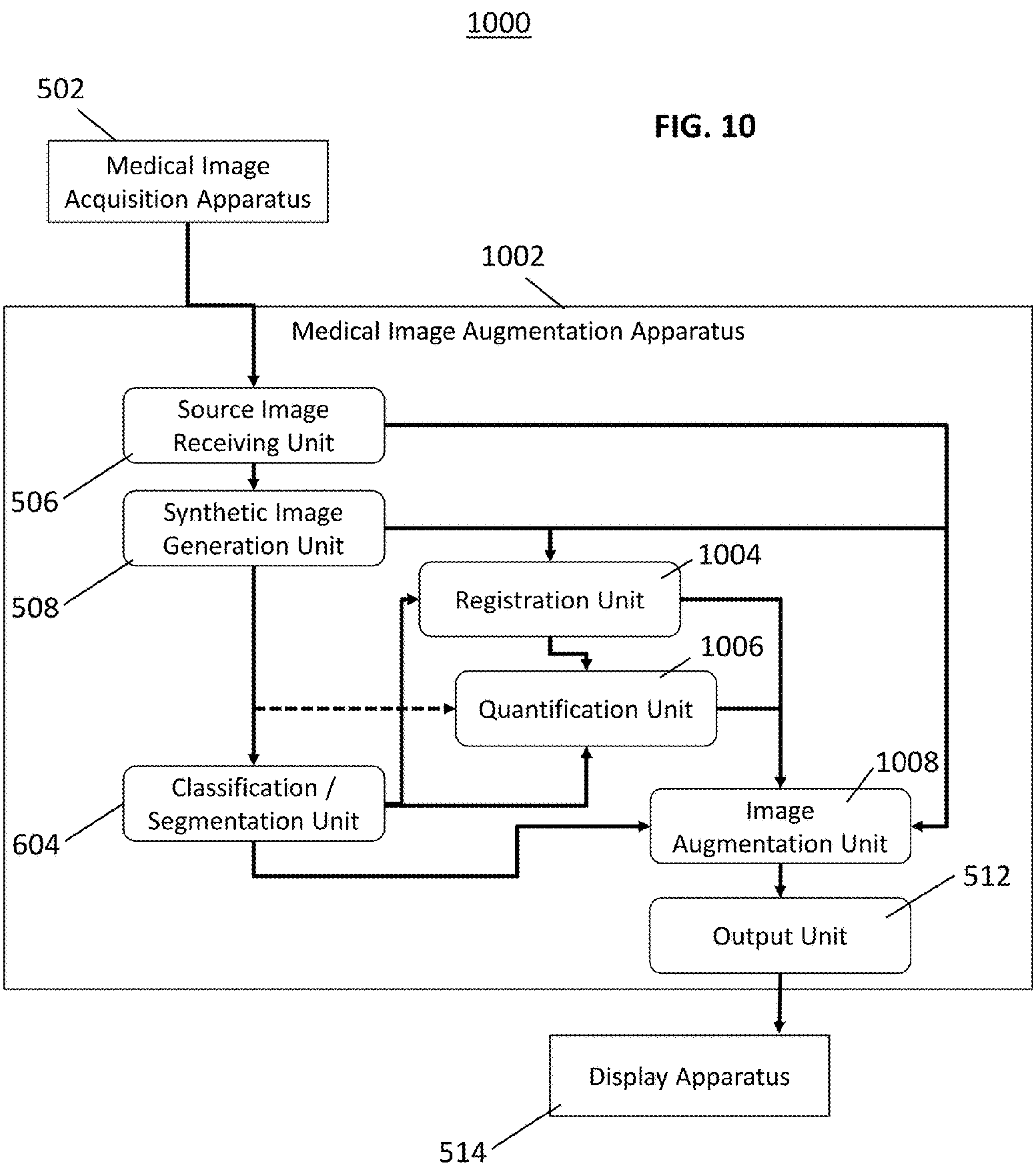
FIG. 10 illustrates an example of a schematic configuration of a medical image augmentation apparatus, according to an embodiment.

In an embodiment depicted in FIG. 10, the medical image augmentation apparatus 1002 comprises the elements of the medical image augmentation apparatus 902 of FIG. 9, further comprising the classification/segmentation unit 604 of FIG. 6. The outputs of the segmentation/classification unit 604 are utilized as inputs to the registration unit 1004, the quantification unit 1006, and the image augmentation unit 1008. In an embodiment, the registration unit 1004 processes the outputs of the classification/segmentation unit 604 and the synthetic image generation unit 508 to measure and compare correspondence between each input and one or more a priori models of the target anatomy in order to increase registration accuracy. In an embodiment, the quantification unit 1006 processes the outputs of the registration unit 1004, the synthetic image generation unit 508, and the classification/segmentation unit 604, to generate more accurate anatomical metrics. In an embodiment, the image augmentation unit 1008 processes the outputs of the source image receiving unit 506, the synthetic image generation unit 508, the registration unit 1004, the quantification unit 1006, and the classification/segmentation unit 604, to generate an augmented image that contains graphical overlays with increased accuracy in anatomical alignment and increased accuracy in metrics conveyed in graphical overlays.

Figure 11:
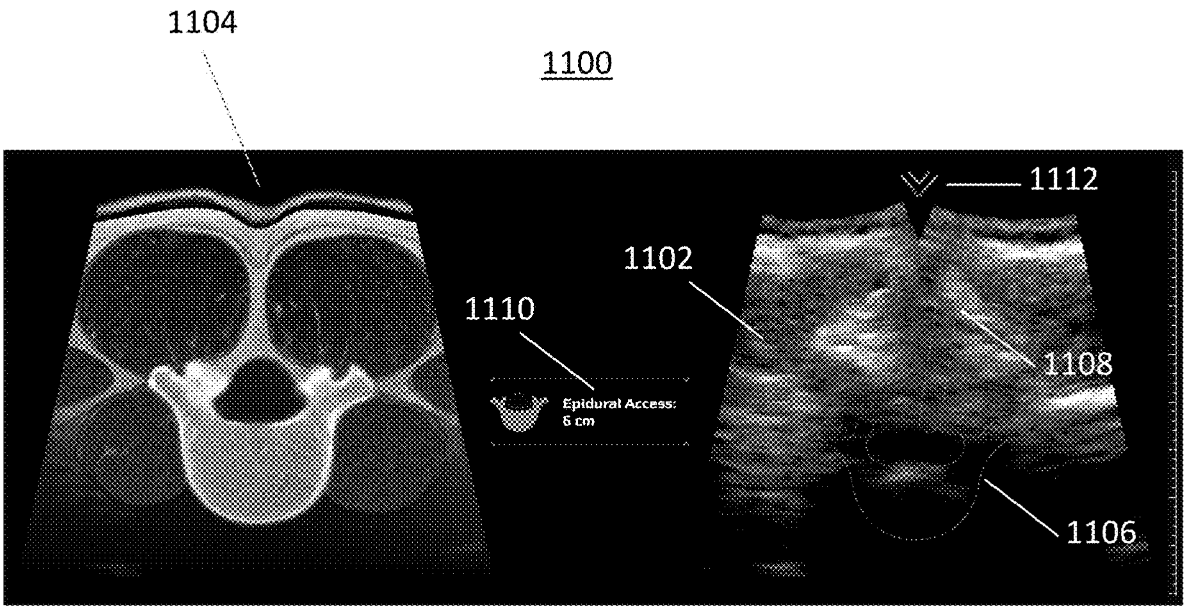
FIG. 11 depicts an exemplary augmented medical image of a lumbar spine that includes registration with an anatomical model and associated quantitative metrics, in accordance with one or more embodiments.

FIG. 11 illustrates an exemplary embodiment of the medical image augmentation apparatus described in FIG. 9. The augmented image 1100 contains a graphical representation 1104 of the anatomy based on an a priori model of a lumbar spine comprised of a CT/MRI image fusion that corresponds to the anatomical cross section that is contained in the source image 1102. In this non-limiting example, the image augmentation unit 906 also renders line-art overlays 1106 derived from the registration to the a prior model to depict outlines of bone anatomies, needle guidance overlays 1108 that provide trajectory guidance to the location of the epidural space in the a priori anatomical model, measurement information 1110 to relate the depth to anatomical target of the needle guidance procedure, in this example, the epidural space, and midline overlays 1112 that provide information on spatial alignment of the anatomy relative to the imaging device.

Figure 12:
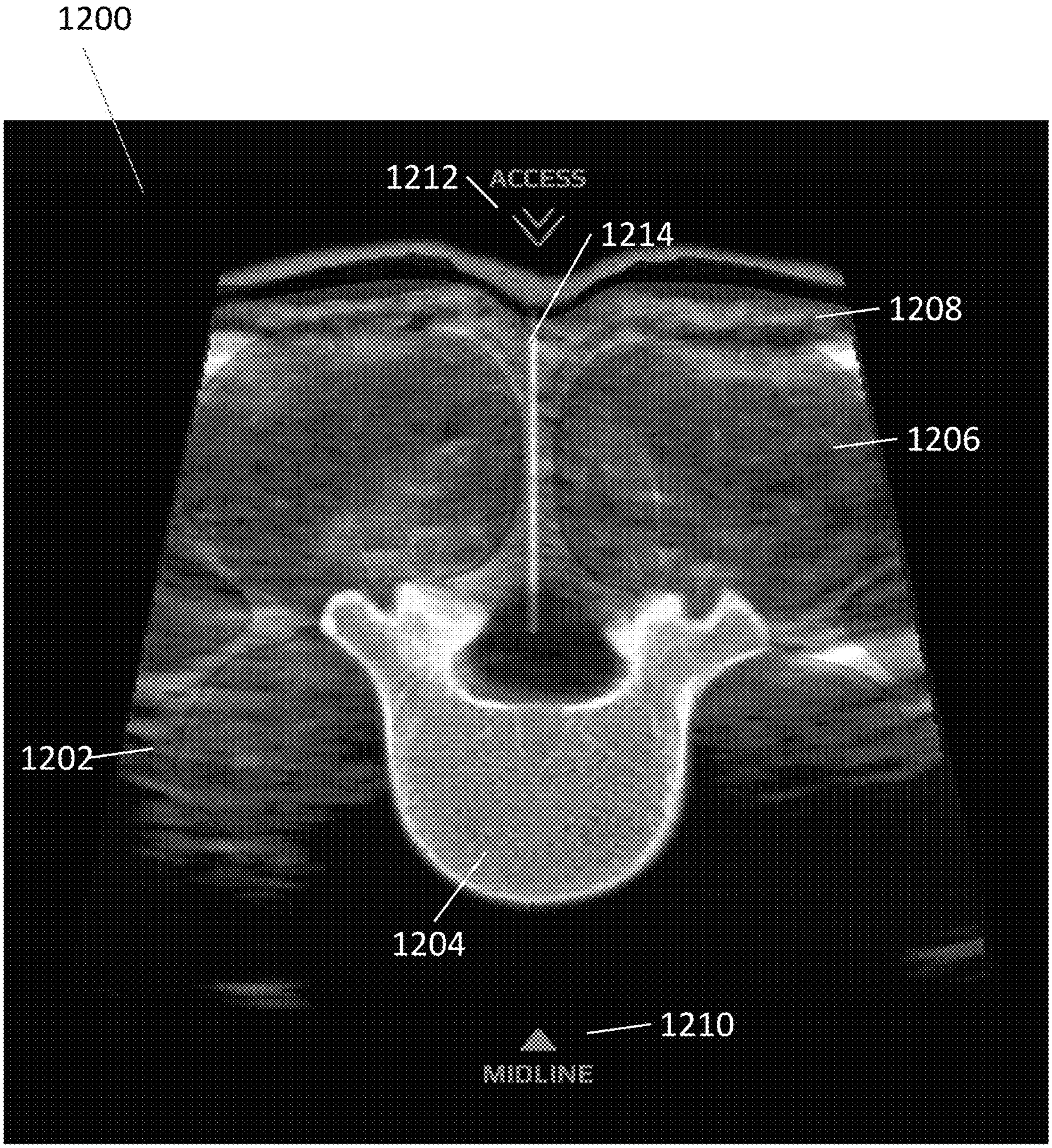
FIG. 12 depicts an exemplary augmented medical image of a lumbar spine that includes registration with an anatomical model and associated quantitative metrics, in accordance with one or more embodiments.

FIG. 12 illustrates an exemplary embodiment of the medical image augmentation apparatus described in FIG. 10. In this embodiment, the augmented image 1200 contains a synthesis of anatomical information derived from the synthetic image generation unit 508, the registration unit 1004, the segmentation/classification unit 604, and the quantification unit 1006. In this non-limiting example, the augmented image is comprised of the synthetic image 1202 of a lumbar spine, a computer-generated bone overlay 1204 derived from an a priori CT model of the lumbar spine, a computer-generated shaded overlay corresponding to the location of adipose tissue 1208 in the synthetic image 1202 based on segmentation from the classification/segmentation unit 604, a computer-generated shaded overlay corresponding to the location of muscle 1206 in the synthetic image 1202 based on a combination of outputs from the classification/segmentation unit 604 and the registration unit 1004, a graphical indicator depicting the location of the spine midline 1210 based on the output of the quantification unit 1006, a graphical indicator depicting the location of needle access corresponding to the preferred needle trajectory for accessing the epidural space 1212 based on a combination of outputs from the registration unit 1004 and the quantification unit 1006, and a graphical indicator depicting the current location of the needle in the ultrasound image 1214 based on the output of the quantification unit 1006.

Embodiments of the invention also include a computer readable medium comprising one or more computer files comprising a set of computer-executable instructions for performing one or more of the calculations, steps, processes, and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

As used herein, the term "about" refers to plus or minus 5 units (e.g., percentage) of the stated value.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that while certain of the illustrations and figure may be close to the right scale, most of the illustrations and figures are not intended to be of the correct scale.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

The invention claimed is:

1. A computerized method for electronically generating an augmented digital image of an anatomical region of a subject, the computerized method comprising:

receiving a source image of the anatomical region of the subject, the source image acquired by an electronic imaging device using a source imaging modality;

generating a synthetic image using a trained machine learning model trained on a plurality of images having known anatomical features and locations based on the anatomical region in the source image, wherein the synthetic image contains at least one synthetic anatomical feature of the imaged anatomical region that can be determined from an anatomical model of the anatomical region of the subject using the trained machine learning model, and wherein the at least one synthetic anatomical feature of the anatomical region of the subject is an anatomical feature that should appear in the source image but is partially or totally obscured and/or distorted in the source image;

partially or completely combining the source image and the synthetic image to produce the augmented digital image; and using a trained machine learning network that classifies regions of the augmented image as corresponding to bone anatomy, muscle anatomy, vascular anatomy, adipose anatomy, or other anatomy, to produce a spatial classification map, wherein the spatial classification map is spatially registered to at least one a priori anatomical model to determine at least one quantitative measure related to the anatomical region of the subject.

2. The computerized method of claim 1, wherein the synthetic image has an appearance of being acquired by an electronic imaging device that is the same or similar to the electronic device capturing the source image.

3. The computerized method of claim 1, wherein the source imaging modality is one or more of ultrasound, MRI, CT, OCT, X-Ray, and photoacoustic imaging.

4. The computerized method of claim 1, wherein the augmented digital image is updated in real-time as a user of the electronic imaging device is altering the position of the electronic imaging device relative to the anatomical region of the subject.

5. The computerized device of claim 1, wherein combining the source image and the synthetic image comprises blending, overlaying, compounding, merging, and/or overlapping the source image and the synthetic image.

6. The computerized device of claim 1, wherein the source image and/or the synthetic image is a still image, a video image, a two-dimensional image, and/or a three-dimensional image.

7. The computerized method of claim 1, wherein the at least one synthetic anatomical feature of the anatomical region of the subject is one or more bone surface that is not found in the source image or is distorted or obscured in the source image.

8. The computerized method of claim 1, wherein the at least one synthetic anatomical feature of the anatomical region of the subject is a soft-tissue structure of a neuraxis.

9. The computerized method of claim 1, wherein the trained machine learning model is a trained generative adversarial network.

10. The computerized method of claim 9, wherein the trained generative adversarial network is based on at least one of a U-Net, a context encoder, and a variational autoencoder.

11. The computerized method of claim 1, wherein the trained machine learning model is further trained using a simulated synthetic dataset containing anatomical features that are partially or totally obscured in a source dataset.

12. The computerized method of claim 11, wherein the simulated synthetic dataset is generated by incorporating anatomical information that is not present in the source dataset by referencing at least one synthetic a priori anatomical model.

13. The computerized method of claim 11, wherein the simulated synthetic dataset is generated by incorporating data from an imaging modality including one or more of ultrasound, computed tomography, magnetic resonance, x-ray, and multi-modality fusion.

14. The computerized method of claim 1, wherein the spatial classification map is applied to and/or combined with the source image or augmented digital image to improve visualization of at least one predetermined classification.

15. The computerized method of 14, wherein the improved visualization is generated by altering pixel intensity, coloration, texture, lighting, or a combination thereof.

16. The computerized method of claim 1, wherein the spatial classification map is processed to determine at least one quantitative measure related to the anatomical region of the subject.

17. The computerized method of claim 16, wherein the at least one quantitative measure is one or more of a distance measurement, a dimensional measurement, or a positional measurement.

18. The computerized method of claim 1, wherein a pose of the augmented digital image is spatially registered to a pose of at least one a priori anatomical model to determine at least one quantitative measurement related to the anatomical region of the subject.

19. The computerized method of claim 18, wherein the at least one quantitative measurement is one or more of a distance measurement, a dimensional measurement, a positional measurement, or a comparison of positional alignment with ideal positional alignment for a more medical procedure.

20. The computerized method of claim 18, wherein the at least one a priori anatomical model is a synthetic anatomical model.

21. The method of claim 18, wherein the at least one a priori anatomical model is composed of data from an imaging modality such as ultrasound, computed tomography, magnetic resonance, x-ray, or multi-modality fusion.

22. The computerized method of claim 1, wherein the source image is provided in a three-dimensional volume, and the augmented digital image is provided in a three-dimensional volume.

23. A computerized method for electronically generating an augmented digital image of an anatomical region of a subject, the computerized method comprising:

receiving a source image of the anatomical region of the subject, the source image acquired by an electronic imaging device using a source imaging modality;

generating a synthetic image using a trained machine learning model trained on a plurality of images having known anatomical features and locations based on the anatomical region in the source image, wherein the synthetic image contains at least one synthetic anatomical feature of the imaged anatomical region that can be determined from an anatomical model of the anatomical region of the subject using the trained machine learning model, and wherein the at least one synthetic anatomical feature of the anatomical region of the subject is an anatomical feature that should appear in the source image but is partially or totally obscured and/or distorted in the source image;

partially or completely combining the source image and the synthetic image to produce the augmented digital image; and using a trained machine learning network that classifies regions of the augmented image as corresponding to bone anatomy, muscle anatomy, vascular anatomy, adipose anatomy, or other anatomy, to produce a spatial classification map, wherein the spatial classification map is spatially registered to at least one a priori anatomical model to determine at least one quantitative measure related to the anatomical region of the subject, and wherein the at least one quantitative measure is one or more of a distance measurement, a dimensional measurement, a positional measurement, or a comparison of positional alignment with ideal positional alignment for a medical procedure.

24. A computerized method for electronically generating an augmented digital image of an anatomical region of a subject, the computerized method comprising:

receiving a source image of the anatomical region of the subject, the source image acquired by an electronic imaging device using a source imaging modality;

generating a synthetic image using a trained machine learning model trained on a plurality of images having known anatomical features and locations based on the anatomical region in the source image, wherein the synthetic image contains at least one synthetic anatomical feature of the imaged anatomical region that can be determined from an anatomical model of the anatomical region of the subject using the trained machine learning model, and wherein the at least one synthetic anatomical feature of the anatomical region of the subject is an anatomical feature that should appear in the source image but is partially or totally obscured and/or distorted in the source image;

partially or completely combining the source image and the synthetic image to produce the augmented digital image; and using a trained machine learning network that classifies regions of the augmented image as corresponding to bone anatomy, muscle anatomy, vascular anatomy, adipose anatomy, or other anatomy, to produce a spatial classification map, wherein the spatial classification map is spatially registered to at least one a priori anatomical model to determine at least one quantitative measure related to the anatomical region of the subject, and wherein the at least one a priori anatomical model is a synthetic anatomical model.

25. A computerized method for electronically generating an augmented digital image of an anatomical region of a subject, the computerized method comprising:

receiving a source image of the anatomical region of the subject, the source image acquired by an electronic imaging device using a source imaging modality;

generating a synthetic image using a trained machine learning model trained on a plurality of images having known anatomical features and locations based on the anatomical region in the source image, wherein the synthetic image contains at least one synthetic anatomical feature of the imaged anatomical region that can be determined from an anatomical model of the anatomical region of the subject using the trained machine learning model, and wherein the at least one synthetic anatomical feature of the anatomical region of the subject is an anatomical feature that should appear in the source image but is partially or totally obscured and/or distorted in the source image;

partially or completely combining the source image and the synthetic image to produce the augmented digital image; and using a trained machine learning network that classifies regions of the augmented image as corresponding to bone anatomy, muscle anatomy, vascular anatomy, adipose anatomy, or other anatomy, to produce a spatial classification map, wherein the spatial classification map is spatially registered to at least one a priori anatomical model to determine at least one quantitative measure related to the anatomical region of the subject, and wherein the at least one a priori anatomical model is composed of data from an imaging modality such as ultrasound, computed tomography, magnetic resonance, x-ray, or multi-modality fusion.

26. A medical image processing apparatus, comprising:

a means for receiving a source image of an anatomical region of a subject acquired by an electronic imaging device;

a means for generating an augmented digital image by combining a synthetic image of the anatomical region of the subject with the source image, wherein the synthetic image is generated using at least one trained machine learning model, and wherein the synthetic image contains at least one synthetic anatomical feature of the anatomical region of the subject that is missing from, obscured, or distorted in the source image based on at least one anatomical model of the anatomical region of the subject;

a means for producing the augmented digital image by partially or completely combining the source image and synthetic image; and a means for outputting the augmented digital image;

wherein the at least one trained machine learning model is trained to classify regions of the augmented digital image as corresponding to bone anatomy, muscle anatomy, vascular anatomy, adipose anatomy, or other anatomy, to produce a spatial classification map, and wherein the medical image processing apparatus further comprises at least one registration unit that spatially registers the spatial classification map to at least one a priori anatomical model stored in a computer memory.

27. The apparatus of claim 26, wherein the synthetic image has an appearance of being acquired by an electronic imaging device that is the same or similar to the electronic device capturing the source image.

28. The apparatus of claim 27, wherein rendering the augmented digital image comprises incorporating at least one computer-generated graphical augmentation comprising at least one computer-generated graphical overlay, computer-generated anatomical measurement, computer-generated anatomical representation, or a combination thereof.

29. The apparatus of claim 28, wherein the at least one computer-generated anatomical representation is derived from ultrasound, computed tomography, magnetic resonance, x-ray images, or a combination thereof.

30. The apparatus of claim 28, wherein the at least one computer-generated anatomical representation is derived from at least one a priori synthetic anatomical model.

31. The apparatus of claim 26, wherein the apparatus renders the augmented digital image to a display.

32. The apparatus of claim 26, wherein the apparatus contains at least one registration unit that spatially registers the augmented digital image to at least one a priori anatomical model stored in a computer memory.

33. The apparatus of claim 26, wherein the source image is provided in a three-dimensional volume and the augmented digital image is provided in a three-dimensional volume.

* * * * *